United States Patent [19]

Slätis et al.

[11] 4,361,144
[45] Nov. 30, 1982

[54] EXTERNAL COMPRESSION FRAME FOR STABILIZING UNSTABLE PELVIC FRACTURES

[76] Inventors: Pär E. V. Slätis, Ripvägen 11, 02700 Grankulla; Erkki O. Karaharju, Soihtupolku 3 A, 00670 Helsinki 67, both of Finland

[21] Appl. No.: 155,765

[22] Filed: Jun. 2, 1980

[51] Int. Cl.³ .............................................. A61F 5/04
[52] U.S. Cl. ................................ 128/92 A; 128/84 B; 128/92 R
[58] Field of Search .................... 128/83, 84 B, 92 A, 128/92 R, 20; 403/378, 379, 91, 87, 161, 164, 156

[56] References Cited

U.S. PATENT DOCUMENTS 1,940,054 12/1933 Herrold .................................. 403/87
3,408,676 11/1968 Cayo ..................................... 403/91
3,865,105 2/1975 Lode et al. ......................... 128/92 R

OTHER PUBLICATIONS

*Injury*, "External Fixation of the Pelvic Girdle with a Trapezoid Compression Frame", Pär Slätis et al., vol. 7, No. 1, Aug. 1975, pp. 53–56.

Primary Examiner—Michael H. Thaler
Assistant Examiner—C. W. Shedd
Attorney, Agent, or Firm—Fleit & Jacobson

[57] ABSTRACT

An external compression frame for the treatment of fractures of the pelvis comprising four bars so interconnected that they form a trapezoidal square. The frame, positioned in an upright position, comprises two vertical and two horizontal bars, connected to each other with articulations. The vertical two bars extend beyond the fastening points of the square to form the part of the frame which is intended for anchoring of the device into the pelvis. The upper horizontal bar has a predetermined length, whereas the lower horizontal bar is adjustable as to its length. By adjusting the length of the lower bar, the angle between the vertical bars may be regulated in such a way, that compression force is exerted on the pelvis, thereby bringing the fractured detached parts firmly together. The novel and principally characterizing features of the frame construction are the trapezoidal shape, the predetermined undisplaceable attachments of the articulations connecting the bars, and the design of the articulations as glide bearings. The device is thus a ready-mounted external frame, ready for use in the expedient treatment of acute pelvic fractures.

7 Claims, 3 Drawing Figures

EXTERNAL COMPRESSION FRAME FOR STABILIZING UNSTABLE PELVIC FRACTURES

Fractures of the pelvis arise from severe blunt impacts on the pelvic girdle, for example in traffic accidents, free falls and industrial accidents. In recent years, the principles of external fixation have been applied in the treatment of these severe injuries: by attaching external interconnected bar elements to the fractured pelvis, the broken parts my be aligned and firmly held in an appropriate position until healing has occured. The results have been encouraging.

Previously known external frame systems for the treatment of pelvic fractures consisted of loose bars and articulations connecting the bars to each other. Various geometric designs have been used. A widely accepted mounting of the external frame is a trapezoidal square arranged to grasp the pelvis like a compression device. The mounting was described by P. Slätis and G. O. Karaharju in the British Journal of Accident Surgery "Injury" 7:53, 1975.

In clinical practice, however, hitherto available frame systems assembled of loose bars and articulations have, in the treatment of pelvic fractures, some disadvantages. One drawback is that the commercially available articulations for connecting the bars are constructed with serrated interfaces. Hence, angular adjustment of the frame takes place stepwise which does not allow for adequate adjustment of the angle between the adjacent bars. Consequently, when applying compression to the trapezoidal frame, a part of the compression force is lost in the assembled frame system and not conveyed to the pelvis as intended.

Another disadvantage in hitherto known frame systems is the surgical difficulty encountered when the external frame has to be mounted from numerous parts while treating an acute injury. The mounting requires more than one pair of hands, an excess of time and considerable dexterity.

The object of the present invention is to eliminate said disadvantages. It relates to a frame for fixing the pelvis, said frame comprising bars being pre-assembled by means of fixedly arranged articulations as to form a trapezoidal square formation known per se. The articulations in the corners of the trapezoid are according to the invention fixed on the bars in a way which precludes any displacement in the direction of the bars, such displacement was not earlier always avoidable. This gives a stable ready made frame which is easy to attach to the injured pelvis. Further, in this invention the articulations are constructed as glide bearings. Owing to the smooth pivoting in the bearings, accurate adjustment of the angles between the bars is made possible. Gradually increasing compression may be exerted on the broken pelvis, thus pressing the broken bone fragments firmly together.

In this respect, the construction according to the invention differs from previously known frames in which, due to the serrated interfaces of the articulations, the angular corrections occured stepwise. The compression frame according to the invention further permits an extremely precise stepless regulation of the compression of the pelvis to which it is anchored. Moreover, due to the firm attachments of the articulations, the frame is stable in the planar position. The frame is easy to attach to the pelvis during the operation. It is strong, does not loose its geometrical shape even under heavy loading, and retains—accurately applied—the alignment of the fracture during the subsequent weeks when fracture union takes place. The stability of the broken pelvis, secured with such a frame, is sufficient to allow the patient to bear weight already some weeks after the injury.

One embodiment of the frame according to the invention will now be described by way of example with reference to the accompanying drawing.

Figure 1:
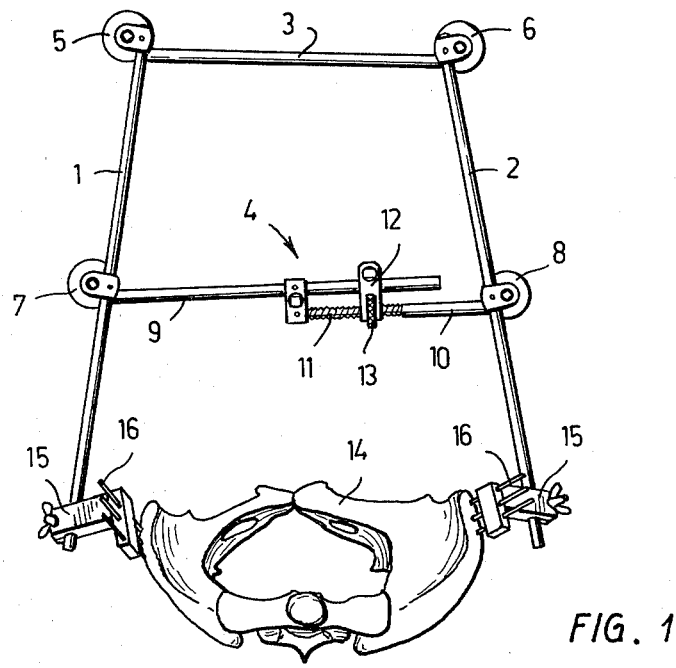
FIG. 1 illustrates a compression frame anchored to a pelvis.

The compression frame comprises two essentially vertical connector bars 1 and 2 and two horizontal transverse bars 3 and 4 connected to the connector bars so that a trapezoidal assembly is obtained. The upper ends of the connector bars are connected to the transverse bar 3 by means of articulations 5 and 6. The ends of the lower transverse bar 4 are connected by articulators 7 and 8 respectively to the connector bars 1 and 2 in points located approximately midway between the ends of the vertical connector bars. The transverse bar 4 is adjustable in its length direction. It comprises two part-bars 9 and 10. The one 10 is provided with threads 11 fitting in a nut 13 connected to the part-rod 9 by means of a support 12. The bars 9 and 10 are displaced in relation to each other by turning the nut 13.

The length adjustment of the bar 4 permits a precise adjustment of the angle between the connector bars 1,2 and 3 and, hence, of the force with which the connector bars 1 and 2 compress the pelvis 14. At their free ends, the connector bars 1 and 2 are in a conventional manner anchored to the pelvis by means of elements 15 and pins 16.

Figure 2:
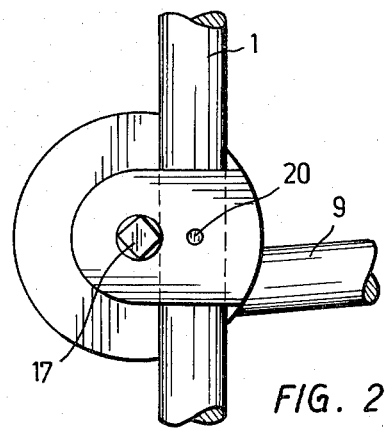
FIG. 2 is a side view of an articulation.
Figure 3:
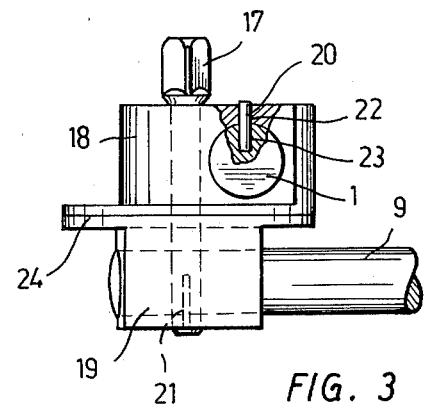
FIG. 3 shows the same articulation in perpendicular projection in relation to FIG. 2.

The articulations 5 to 8 which interconnect the bars 1 to 4 may all be of similar construction. FIGS. 2 and 3 show in an enlarged scale and with reference to articulation 7 in FIG. 1 how these fixtures are constructed. The articulation comprises two elements 18 and 19 pivoting around the pin 17. The elements abut upon each other along two slide surfaces 24 and thus form a glide bearing. The connector bar 1 is fixed in the upper element 18. The part-bar 9 of the transverse bar 4 is fixed in the lower fixture element 18. The bars 1 and 9 extend through holes bored in the respective fixture element. The articulation is therefore undisplaceable in the longitudinal direction of the respective bar as soon as the pins 20 and 21 which extend through said holes are anchored in the respective bars. This pin connection guarantees that the fixture, once fixed in the bars, can no more be displaced before the fixing pins 20 and 21 have been removed from their connecting position. The angle between the vertical and horizontal bars and, hence, the force with which the compression frame compresses the fractured surfaces in the injured pelvis are adjusted by adjusting the length of the bar 4. The formation of the articulations as glide bearings permits precise adjustment of the frame. This has not been possible in earlier known frames.

Finally, it should be noted that the compression frame described above is to be considered as an example. Various equivalent modifications will of course, fall within the scope of the inventive idea. Thus, for example, the pins 20 and 21 may be modified with respect to their thickness and be arranged to be inserted over longer or shorter distances in the bars. The pins may also extend right through the respective bars and they can be threaded for screwing as bolts in threaded holes, etc. The bars may further also be provided with a plurality of holes or recesses for the pins 20,21 placed in a series one after another so that the fixtures, if required, can be fastened at different points of the bars.

The essential features of the frame are: the trapezoidal shape, the predetermined sites of the articulations, the design of the articulations as glide bearing, and the adjustable length of the compression bar placed between the vertical bars.

What I claim is:

1. A compression frame for fixing the pelvis when treating pelvic fractures, said frame, when in an upright position, comprising two substantially vertical bars (1,2) and two substantially horizontal transverse bars (3,4), the vertical bars having lower end portions attached to the pelvis and upper end portions connected to end portions of one (3) of the transverse bars, a second (4) of the transverse bars being adjustable in length and being connected to the vertical bars (1 and 2) so as to form a trapezoidal configuration, articulation means (5–8) for interconnecting said vertical bars and said transverse bars, said articulation means having first and second fixture elements with through bores for receiving respective ones of said bars, said fixture elements being so anchored to the bars that a displacement of the fixture elements in the longitudinal direction of the bars is not possible, said fixture elements while so anchored allowing relative angular movement between the vertical and transverse bars connected by said fixture elements so that the angle between the bars and the compression force exerted by the bars on the pelvis are adjustable.

2. A compression frame as claimed in claim 1, characterized in that the articulation means which connect the bars of the frame are fastened to the bars by means such as pins and screw bolts anchored in recesses or holes provided in the bars.

3. A compression frame as claimed in claim 1 or 2, wherein the articulation means interconnecting the bars enable an adjustment of the angles between the bars, each of said articulation means including glide bearings having main parts abutting each other along slide surface (24), and clamping elements (17) for the fixation of the bearing parts.

4. A compression frame as claimed in claim 1 or 2, characterized in that the second transverse bar (4) consists of two part-bars (9,10) interconnected by means of a thread system, e.g., screw and nut, so that relative rotation of the system parts to each other causes a change of the length of the second bar (4).

5. A compression frame as claimed in claim 3, characterized in that the second transverse bar (4) consists of two-part bars (9, 10), and means including threadedly engaged parts for interconnecting the two-part bars so that relative rotation between the threaded parts causes a change of the length of the second bar (4).

6. A compression frame for fixing the pelvis when treating pelvic fractures, the frame being connectable to connector elements anchored to a pelvis being treated, said compression frame comprising:
a first pair of bars having first end portions connectable to connector elements anchored to the pelvis;
a first transverse bar extending between said first pair of bars and interconnected to second end portions of said first pair of bars;
a second transverse bar extending between said first pair of bars and interconnected to portions of said first pair of bars spaced intermediate said first and said second end portions;
a plurality of articulation means for interconnecting said first and said second transverse bars with said first pair of bars, each of said articulation means having a first fixture element with a through bore formed therein receiving one of the bars, first means for interconnecting said first fixture element with said one bar so that said first fixture element is connected to and fixed in position with respect to said one of the interconnected bars, a second fixture element with a through bore formed therein receiving a second of the interconnected bars, second means for interconnecting said second fixture element with said second bar so that said second fixture element is connected to and fixed in position with respect to said second of the interconnected bars, and means independent from said first and said second means for interconnecting said first and said second fixture elements so as to permit relative movement therebetween to thereby vary the angular relationships between the interconnected bars; and
said second transverse bar being adjustable in length to thereby vary the distance between the first end portions of said first pair of bars whereby the compressive force exerted by said frame on the pelvis is controlled.

7. A compression frame according to claim 6, wherein said second transverse bar comprises:
a first part having one end portion articulated by one of said articulation means to one of said first pair of bars and a threaded end portion extending towards a second of said first pair of bars;
a second part having one end portion articulated by another of said articulation means to the second of said first pair of bars and a second end portion extending towards said one of said first pair of bars; and
means carried by said second part for engaging the threaded end portion of said first part to thereby fix the length of said second transverse bar.

* * * * *